United States Patent
Echizenya

(10) Patent No.: US 6,983,544 B2
(45) Date of Patent: Jan. 10, 2006

(54) METHOD OF MANUFACTURING OPTICAL DEVICE AND INSPECTION GAUGE USED FOR THE SAME

(75) Inventor: Kiyoyuki Echizenya, Hyogo-ken (JP)

(73) Assignee: Toshiba Matsushita Display Technology Co., Ltd., Tokyo (JP)

( * ) Notice: Subject to any disclaimer, the term of this patent is extended or adjusted under 35 U.S.C. 154(b) by 116 days.

(21) Appl. No.: 10/665,476

(22) Filed: Sep. 22, 2003

(65) Prior Publication Data
US 2004/0125367 A1 Jul. 1, 2004

(30) Foreign Application Priority Data
Sep. 19, 2002 (JP) .............................. 2002-274152

(51) Int. Cl.
*G01B 3/14* (2006.01)
(52) U.S. Cl. ....................................... 33/1 BB; 33/563
(58) Field of Classification Search ................. 33/1 B, 33/1 BB, 562, 563, 566
See application file for complete search history.

(56) References Cited

U.S. PATENT DOCUMENTS

| | | | | |
|---|---|---|---|---|
| 1,621,991 A | * | 3/1927 | Mayer | ....................... 33/1 BB |
| 3,109,239 A | * | 11/1963 | Wicker et al. | ............. 33/1 BB |
| 3,266,162 A | * | 8/1966 | Burke | .......................... 33/563 |
| 5,060,388 A | * | 10/1991 | Nys | .......................... 33/1 BB |
| 6,457,250 B1 | * | 10/2002 | Mingus et al. | ................ 33/562 |

* cited by examiner

*Primary Examiner*—Christopher W. Fulton
(74) *Attorney, Agent, or Firm*—Oblon, Spivak, McClelland, Maier & Neustadt, P.C.

(57) ABSTRACT

A rectangular transparent sheet 15 is printed with black dotted density patterns 21 and 22. Each dot of the patterns 21 and 22 is 30 μm in size while dotted area occupied rates of the patterns 21 and 22 range from 3% to 45%. The density patterns 21 and 22 are used for density level assessment of unevenness on a flat panel display device as standard references. Such density level assessment is carried out by comparing the unevenness with the patterns 21 and 22 or by visual inspection with the latter placed on the former.

16 Claims, 4 Drawing Sheets

DOT OCCUPIED RATE OF 3%

DOT OCCUPIED RATE OF 45%

METHOD OF MANUFACTURING OPTICAL DEVICE AND INSPECTION GAUGE USED FOR THE SAME

FIELD OF THE INVENTION

This invention relates to a method of manufacturing an optical device and an inspection gauge used for such a method of manufacturing an optical device.

BACKGROUND OF THE INVENTION

Flat panel display devices, e.g., liquid crystal display devices, are widely used as those for personal computers, word processors, television receivers, etc. and projection type display devices as well because the display devices have the advantage of thin thickness, light weight or low power consumption.

Since active matrix type liquid crystal display devices, in particular, provided with switching elements connected to pixel electrodes have an excellent display without any substantial cross-talk between adjacent pixels, they have been vigorously researched and developed.

In manufacturing the flat panel display device, the snapping or short circuits of wirings or electrically conductive patterns and display defects, such as uneven brightness or chromaticity caused by dusts and/or partial defects, are inspected at the completion of a display panel unit or display module of the flat panel display device. In general, test signals are applied from signal line and scanning line pads to observe image display conditions of pixels for the detection of such defects as set forth above. Since these inspections are carried out during the time when a light source is turned on, these are called "turned-on tests".

There have been various disclosures as to an automatic image processing system provided with a CCD camera for such turned-on tests (see, e.g., Japanese Laid-Open Patent Application Tokkaihei 8-145848 and Japanese Laid-Open Patent Application Tokkaihei 11-101712). It is easy to detect and judge the snapping or short circuits of wirings and electrically conductive patterns or black spots (disabled pixels) but relatively difficult to judge if uneven brightness (unevenness in light and shade) in spot regions or the like is within the tolerance. Thus, the automatic image processing system at present is second only to visual tests by skilled inspectors in the efficiency and accuracy of detection and/or judgment for subtly uneven display.

The assessment of uneven brightness such as its degree (density) and number appearing on the display panel is of critical importance as to the determination of whether the flat panel display device is good and in shippable quality or not. Inspectors are required to be highly skilled in such assessment while less skilled inspectors are often commit assessment errors.

The visual tests for the determination of uneven brightness is carried out in one of the following ways:

(1) One display panel with certain uneven density slightly exceeding the tolerance (a boundary sample for a bad quality panel) or another with unevenness barely within the tolerance (a boundary sample for a good quality panel) are used for comparison standards of reference The determination as to whether a display panel under inspection is good or bad is made in comparison of such a display panel with those samples.

(2) A neutral density (ND) filter with specific transmittance is placed on uneven display portions of a display panel under inspection to check whether any uneven display can be seen or not. If no substantial unevenness is seen, the display panel is judged to be good. Otherwise, it is judged to be bad.

(3) In order to display specific density unevenness an inspection signal is supplied to a display panel under inspection from an inspection device for the "turned-on tests". In other words, the display panel is driven to display image patterns similar to unevenness by using software programs. The inspector can determine if the uneven display by the display panel is within the limit of tolerance for density.

Patent publication reference No. 1: Japanese Laid-Open Patent Application Tokkaihei 8-145648.

Patent publication reference No. 2: Japanese Laid-Open Patent Application Tokkaihei 11-101712.

The inspection methods of unevenness set forth above have the following problems:

(1) The inspection method by means of boundary samples

First, appropriate samples with specific uneven densities are rarely found.

Secondly, two independent sets of flat panel display devices are necessary to operate a display panel under inspection and a boundary sample at the same time for the benefit of efficient inspection. Where, however, only one set of the flat panel display device is available, the boundary sample and the display panel under inspection are driven separately or alternatively to compare the former with the latter while relying on the remembering of displays of the boundary sample implemented as reference displays by the former. The inspectors must be well-trained to avoid possible judgment errors.

Further, the reference displays on the sample do not remain unchanged but become fainter with a lapse of time. It is necessary to check the boundary sample regularly in a certain period of time. In short, the periodic checking of the reference displays is required, accordingly.

(2) The inspection method by means of ND filters

Since this method is strongly influenced by ambient illumination at working places, the illumination must be strictly controlled.

In addition, market available ND filters have large dispersion in transmittance. Thus, even if the illumination is strictly controlled, the inspections have dispersion in their results caused by the dispersion in transmittance of the ND filters.

(3) The inspection method by means of software programmed patterns similar to unevenness Display panels such as liquid crystal display panels have viewing angle characteristics so that the uneven density patterns are subject to sharp changes with respect to viewing angles.

SUMMARY OF THE INVENTION

It is an object of this invention to provide a method of manufacturing an optical device to precisely assess defects of unevenness appearing on a main surface of the optical device and an inspection gauge used for the same.

According to one aspect of the present invention, a method of manufacturing an optical device includes placing an inspection gauge on a main surface of the optical device, the inspection gauge being provided with a density pattern formed on a transparent sheet or film, and comparing optical unevenness of the optical device with the density pattern of the inspection gauge in light of a density level to determine whether the optical unevenness is lighter or darker in density than or equal to the density pattern of the inspection gauge.

In the method of manufacturing an optical device the optical device projects light from the main surface when the optical device is enabled.

The inspection gauge is placed on the main surface of the optical device in order for the density pattern to be next to the optical unevenness.

The inspection gauge is also placed on the main surface of the optical device in order for the density pattern to cover the optical unevenness.

A method of manufacturing an optical device according to the present invention is characterized in that the inspection gauge includes a plurality of different degrees of density patterns. The different degrees of density patterns are disposed in order of density degrees.

A method of manufacturing an optical device according to the present invention is further characterized in that the different degrees of density patterns are compared with the optical unevenness to assess visually difference between the different degrees of density patterns and the optical unevenness.

The density pattern is made of dots provided on the sheet or film and the density degree is expressed by the number of dots occupied per unit area or dot occupied rates.

The dots are uniformly dispersed discrete circles or rectangles and are of a predetermined size, which is less than or equal to 40 $\mu$m.

A method of manufacturing an optical device according to the present invention is characterized in that the inspection gauge includes density patterns with different dot occupied rates and the dot occupied rates range from 3% through 45%. The density patterns of the inspection gauge include low density degrees each defined by a discretely additional and predetermined dot occupied rate ranging from 1% to 3% and high density degrees each defined by a discretely additional dot occupied rate of 5%.

An optical device manufactured by a method of the present invention is a display panel or an illumination apparatus.

According to the present invention, an inspection gauge to assess optical unevenness on a main surface of an optical device is provided with a transparent base sheet or film, and a density pattern is provided on the base sheet or film and made of a set of dots which are less than or equal to 40 $\mu$m in size.

This patent application is based upon and claims the benefit of priority from the Japanese Patent Application No. 2002-274152, filed on Sep. 19, 2002, the entire contents of which are incorporated herein by reference.

BRIEF DESCRIPTION OF THE DRAWINGS

A more complete appreciation of the present invention and many of the attendant advantages thereof will be readily obtained as the same becomes better understood by reference to the following detailed descriptions when considered in connection with the accompanying drawings, wherein.

DETAILED EXPLANATION OF THE PREFERRED EMBODIMENTS

An inspection gauge according to an embodiment of the present invention is provided with a density pattern formed on a transparent and colorless sheet or film. The density pattern is made of a set of dots which each are less than or equal to 40 $\mu$m in size.

Any sheet or film (hereinafter called the "sheet" including a thin sheet or film) can be used if the sheet has appropriate transparency (transmittance and haze) and durability as a base film. The sheet is preferably transparent and colorless and made from olefin system resins such as poly methyl pentene resin, saturated polyester system resins such as polyethylene terephtbalate (PET) or polyethylene naphthalate, methacrylic resins, or acrylic resins and its thickness ranges from 50 $\mu$m to 500 $\mu$m. Where a transparent and colorless sheet is employed as a density pattern base, the inspection gauge is capable of examining not absolute density but the degree of optical unevenness with respect to a background color of the optical device.

On this transparent base sheet, display patterns with various degrees of density are printed by applying an ordinary printing method such as photolithography or the like. Further, the base sheet is subject to prior treatment to improve its printing properties, if necessary. Other methods such as ink-jet printing and offset printing may be used to draw display patterns with desired degrees of density on the base sheet.

The display patterns are preferably uniform distributions of dots (meshes) which are individually discrete circles, rectangles or the like. Each degree of density is expressed in accordance with an occupied rate of dots per area of places where the display patterns are provided. The dots may be checkered and the like.

The dots each are preferably black in color and less than 40 $\mu$m in size or, more preferably, 20 $\mu$m to 35 $\mu$m because Moire fringes may appear inversely affecting display quality if the dot size is more than 40 $\mu$m. On the other hand, if the dot size is less than 20 $\mu$m, it is not desirable because costs for making the display patterns by printing, etc. increase and it does not yield any significant functions.

Figure 1:
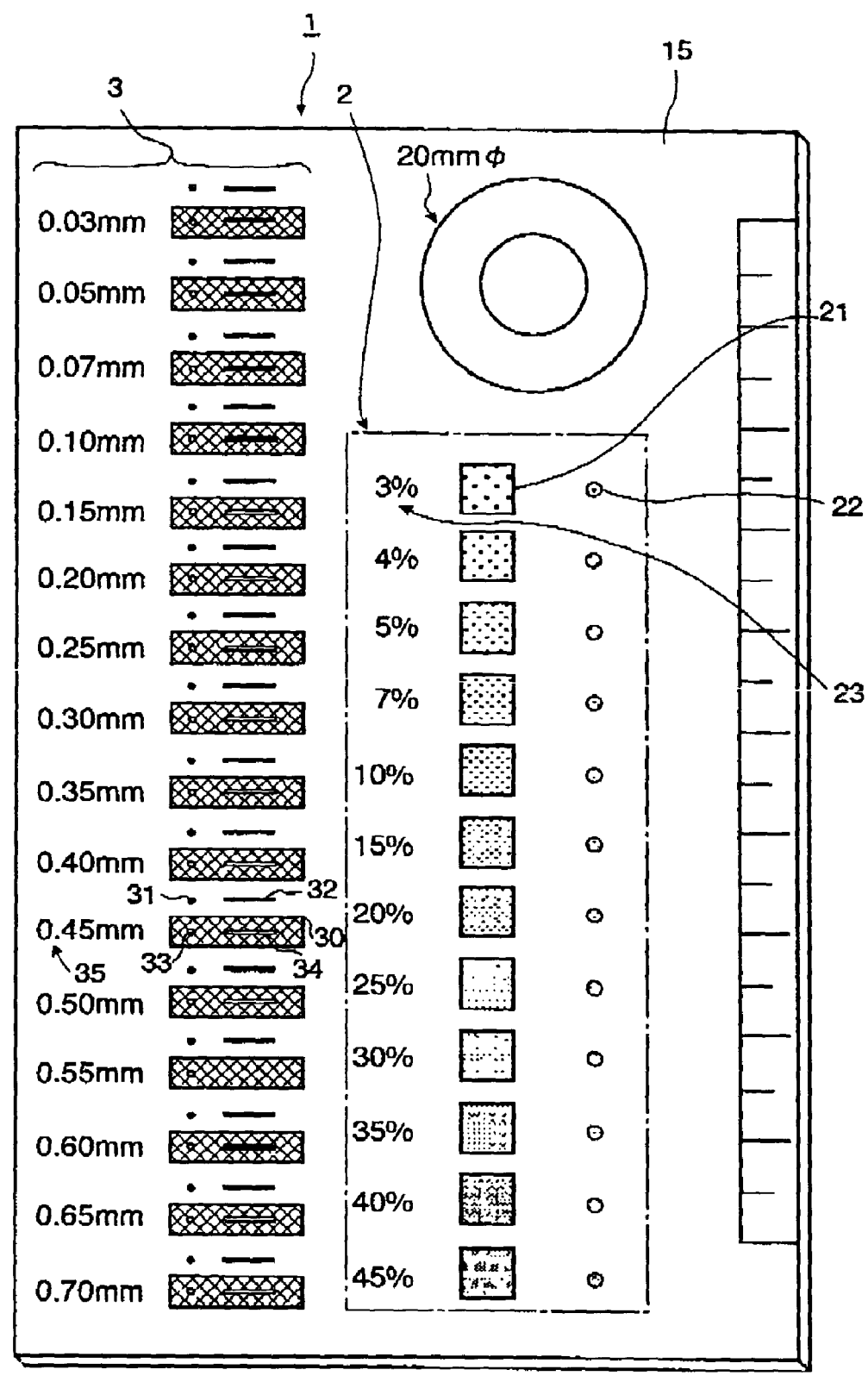
FIG. 1 is a plan view of an inspection gauge of the present invention.

At least one density pattern is necessary for the gauge of the present invention but density patterns with different degrees are preferably provided for it. In other words, if the tolerance of optical unevenness remains unchanged, at least one density pattern may be used for assessment of the optical unevenness but, otherwise, density patterns with different degrees should be provided to assess the optical unevenness. For that purpose, discrete degrees of density patterns may be prepared for the assessment of different degrees of optical unevenness as measuring scales.

Where different degrees of density patterns are formed, each of them is preferably disposed in order of degrees or levels of density. Based upon them, it is possible to assess the degree of which the optical unevenness is. A discretely additional degree of density ranges from 1% through 3% for the degrees of density in the vicinity of a tolerance or permissible value, such as 3% through 10% shown in FIG. 1, i.e., the range from 3% through 10% being shown in 1%, 2% or 3% increments, while the discretely additional degree is 5% up to a degree of density of 45% such as 10% through 45% also shown in FIG. 1 shown in increments of 5% in FIG. 1.

With those arrangements for the inspection gauge, it is much easier to examine the optical unevenness than in the case of inspection gauges individually prepared for different degrees of density. It is possible not only to detect the unevenness but also to take measures in relation to its degrees.

The inspection gauge of the present invention is preferably provided with additional patterns to measure or assess sizes of optical unevenness. Such additional patterns are made of slits or lines with predetermined widths, rectangularly or circularly cut-out patterns with predetermined sizes provided in background patterns, or size assessment patterns provided in rectangular or circular background patterns.

Assessment or determination of optical unevenness by means of the inspection gauge can be carried out by detecting the unevenness of prospective ones and by comparing them with the density patterns to check whether the former is equal in density distribution to the latter.

Figure 4:
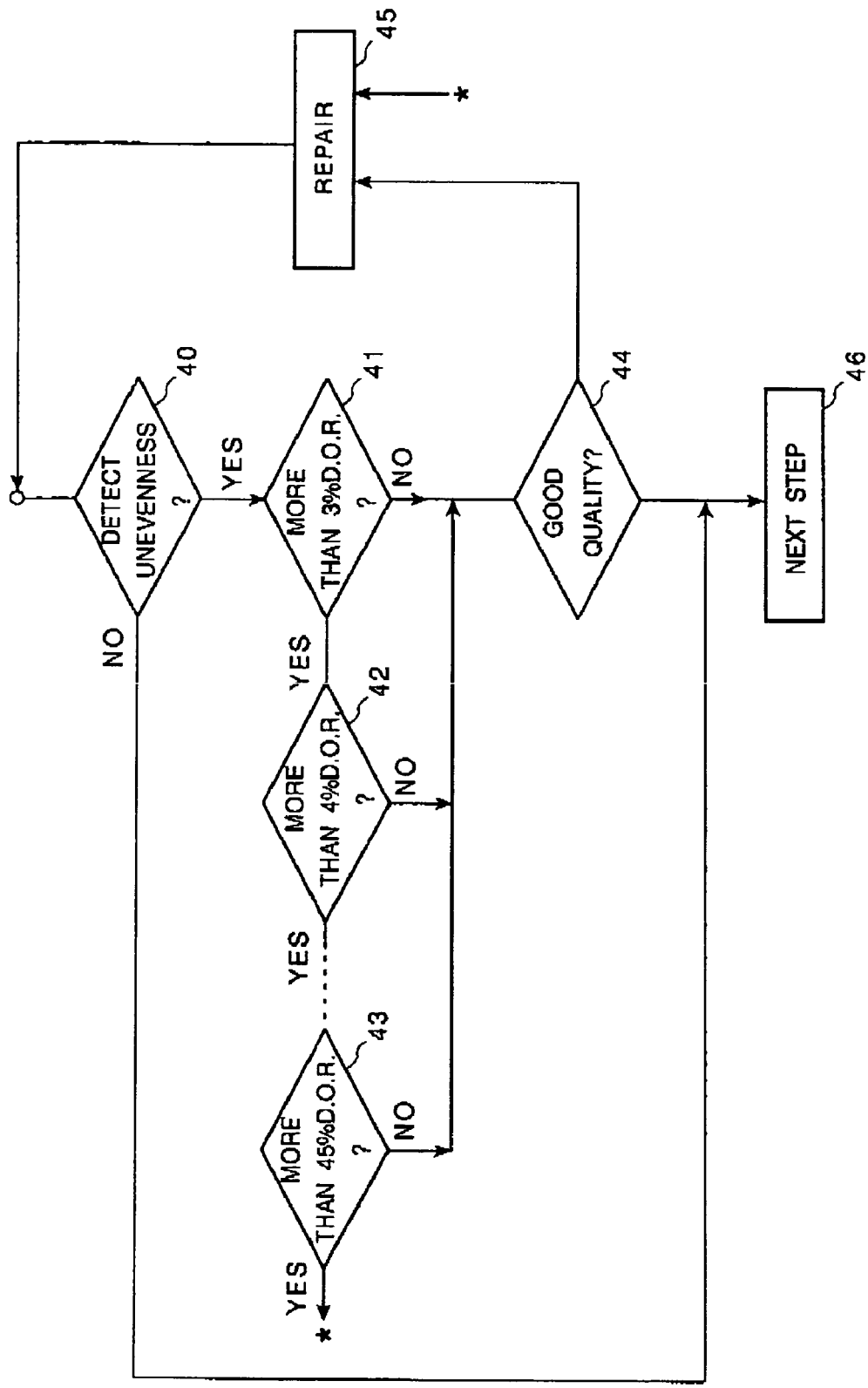
FIG. 4 is an assessment flowchart of a method of manufacturing an optical device.

With reference to FIG. 4, permissible degrees of density or degrees of density within tolerance each are set for sizes of unevenness. Where optical unevenness of a display device under inspection is detected in step 40, its degree of density is checked in steps 41 through 43 as to whether it is within the limit of tolerance or not (steps 41 and 42 may start with, and carry out, the judgments of a dot occupied rate (D.O.R.) of 10%, for example, and an appropriate D.O.R., such as 15%, 20%, or the like, respectively). If it is not within the limit of tolerance, the optical device is transferred to repair step 45. If it is within the limit of tolerance, however, it is further inspected as to whether the number of unevenness complies with a requirement in step 44. Alternatively, the unevenness in question may be also judged as to whether the number of optical unevenness per display panel multiplied by coefficients determined in accordance with sizes and degrees of density of such unevenness is more than a setting value of tolerance or not.

Figure 5:
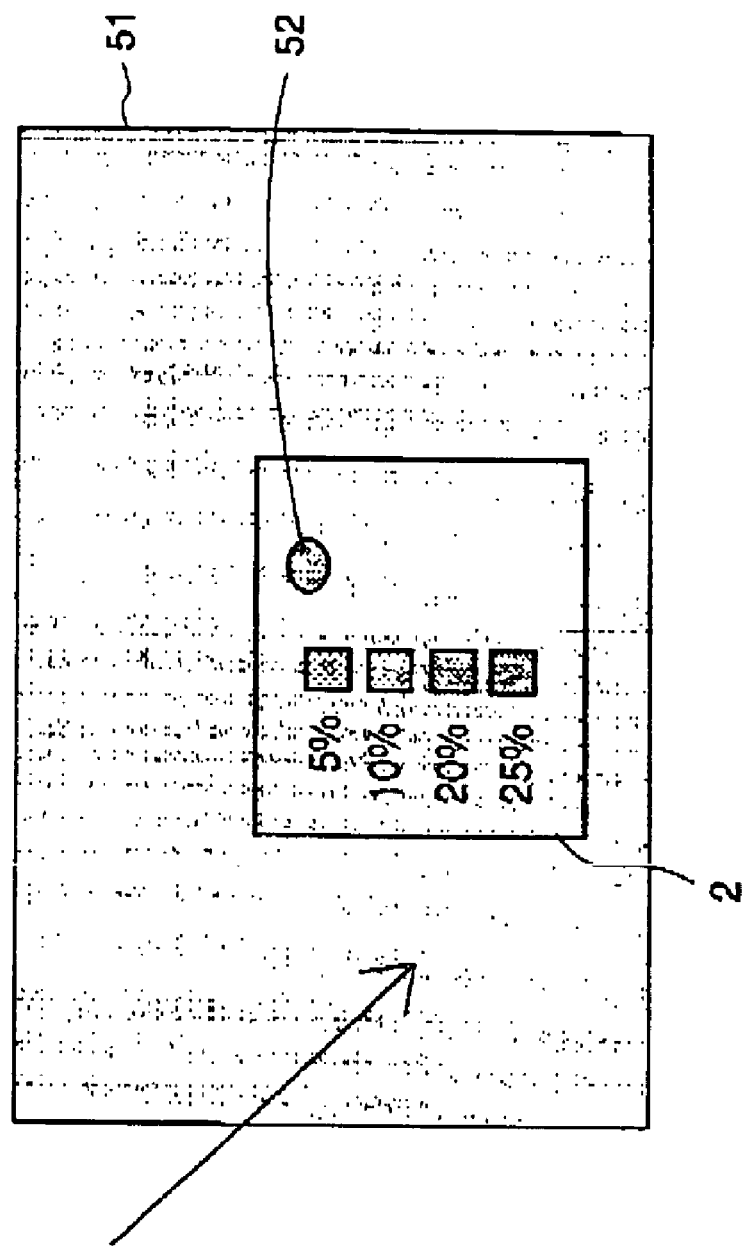
FIG. 5 is a schematic plan view of an inspection gauge placed on a main surface of an optical device according to another embodiment of the invention.
Figure 5:
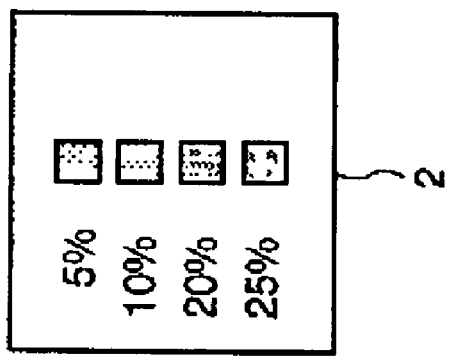

As shown in FIG. 5, for easy comparison, density gauge 2 may be placed on a main surface 51 of an optical device, i.e., a projection surface of a display device to set an appropriate density pattern next to unevenness 52. Since density patterns 21 (shown in FIG. 1) of density gauge 2, in particular, are disposed in a column direction in the order of discretely different density levels (degrees), unevenness 52 can be placed next to, and compared with, a series of density patterns 21 to determine easily and quickly whether unevenness 52 is permissible or not.

Instead of the determination set forth above, the density patterns are placed on the unevenness to assess its density by checking whether the unevenness can be visually observed or not. In this case, the assessments of the unevenness under inspection can be carried out easily and promptly by placing a series of the discretely different density patterns on the unevenness.

Those comparison tests or overlapping inspections can be also done while observing the reference patterns and the unevenness through a loupe or a stereoscopic microscope. In some cases, an image analyzing system may assess the degree of visibility of the unevenness overlapped with the density patterns.

The inspection of unevenness can be implemented during the turned-on tests before a tape carrier package (TCP) or a driving printed circuit board (PCB) is assembled with it or after that (i.e., completion of a display panel). However, it may be done even after a rear light source is assembled with a display panel.

Further, a circuit array substrate or a counter substrate of a flat panel display device may be manufactured in accordance with the methods disclosed in Japanese Patent Disclosure Tokkaihei Nos. 9-160076, 2000-267595, 2000-330484 or 2001-339070.

The inspection gauge of the present invention is applicable not only to a liquid crystal display device but also to an organic electro-luminescence (EL) type display device and the like. Assessment of the degree of density can be brightness levels for white display as well as those for color display. In the latter case, the density patterns may be provided for patterns of a specific color. Where black dots are employed as in the present embodiment, it is desirable to assess the unevenness in the state of a half-tone display and, more specifically, in a gray color display in this case.

Unevenness under inspection is generally caused by foreign bodies but, regardless of causes, they may be of any other unevenness or irregularities as far as they are similar to each other. The unevenness is not limited to spot-like ones but may also be line-like unevenness An inspection gauge of an embodiment of the present invention will be explained below with reference to FIGS. 1–3.

As shown in FIG. 1, inspection gauge 1 is provided with density gauge 2 for the assessment of density of unevenness and size gauge 3 for the measurement of approximate sizes arranged on the right and left halves of rectangular transparent sheet 15, respectively.

The density gauge 2 includes screen tone-like printed patterns (density patterns 21 and 22) provided in a row direction to indicate various degrees of density (brightness levels). As a concrete example, pairs of 5 mm long square patterns 21 and 0.5 mm diameter circular patterns 22 on their right side are disposed in a row direction. The square and circular patterns 21 and 22 provided at the same levels are the same in density. The pairs of the patterns 21 and 22 have 12 levels of density, i.e., dot-occupied rates ranging from 3 percent (%) to 45 percent (%) as indicated by the figures.

Figure 2:
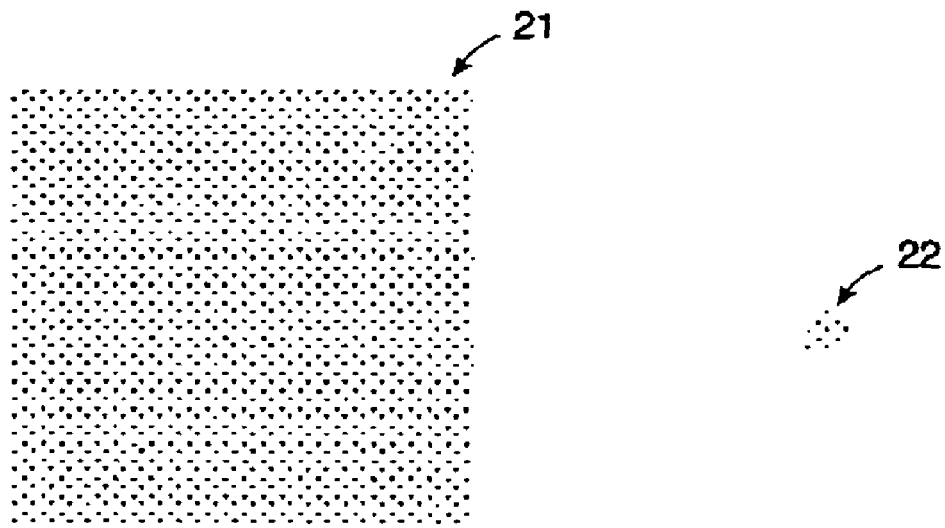
FIG. 2 is a magnified screen-tone pattern (density pattern) with a dot occupied rate of 3% in the inspection gauge shown in FIG. 1.
Figure 3:
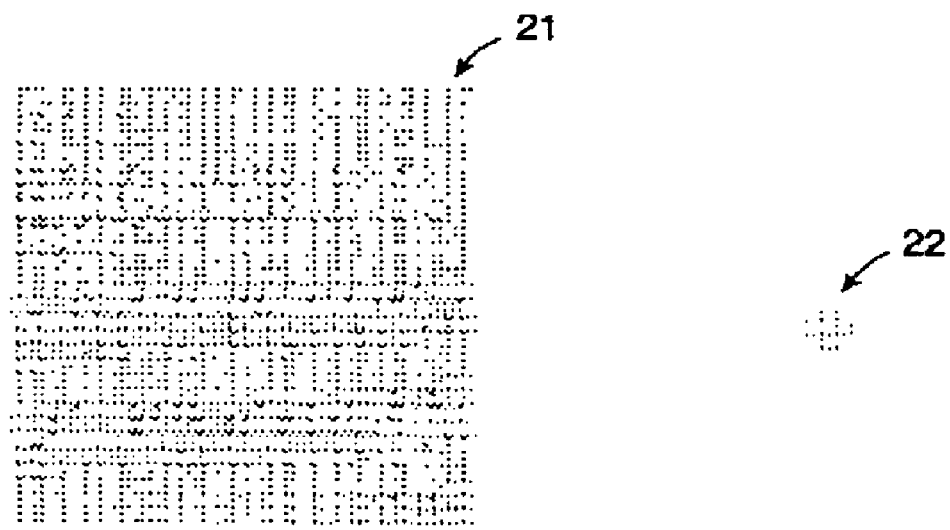
FIG. 3 is another magnified screen-tone pattern (density pattern) with a dot occupied rate of 45% in the inspection gauge shown in FIG. 1.

FIGS. 2 and 3 show pairs of magnified density patterns 21 and 22 with dot-occupied rates of 3% and 45%, respectively. Each dot of the density gauge 2 found in patterns 21 and 22 in the embodiment is an independent circle with a diameter of 30 μm.

On the left of density patterns 21 there are printed indications 23 of dot occupied rates. Since the pattern contour is rectangular and circular in shape in each level of density pattern, appropriate sizes and degrees of density patterns are used to examine the unevenness so that the assessment accuracy can be improved.

Size gauge 3 is disposed to quickly measure and assess unevenness on the left side of transparent sheet 15. Size gauge 3 is provided with 16 sets of size patterns which are rectangular blocks 30 and size display patterns 31 and 32. Rectangular blocks 30 each include portions to define small rectangularly or circularly cut-out patterns 33 and slits 34. Size display patterns 31 and 32 and dotted patterns and slit 34 range from 0.03 mm to 0.70 mm as shown in FIG. 1. On the left of the rectangular blocks there are printed size indicators 35.

When sizes of unevenness are measured with size gauge 3, inspection gauge 1 is positioned to make rectangularly or circularly dotted patterns 31 or linear patterns 32 next to the unevenness. When this operation is repeated and determines that rectangular or circularly dotted pattern 31 or linear pattern 32 fit the unevenness, its size indicator 35 on the left is read and recorded as the size of the unevenness. Alternatively, inspection gauge 1 is also placed to put the unevenness into rectangularly or circularly cut-out patterns 33 or slits 34 to measure their size.

Tables 1 and 2 show assessment results on effects obtained from the method for inspecting unevenness by means of the inspection gauge (the "Embodiment") and the boundary sample (the "Comparison").

Table 1 sets forth an average correct judgment rate (the "Correct Rate") in the case that differently skilled inspectors have judged whether 10 sample display panels are good or not in a predetermined short period of time. Judgment error rate data are also described in Table 1 in which the data at a judgment error rate of good samples (the "Overkill Rate") mean that good display panel samples are erroneously judged bad and those at a judgment error rate of bad samples (the "Short Rate") mean that bad display panel samples are erroneously judged good. Further, test results based on prior art boundary samples under the same conditions are set forth in Table 1 as comparison data.

TABLE 1

ASSESSMENT OF JUDGMENT ERROR RATES

|  | Correct Rate | Overkill Rate | Short Rate |
| --- | --- | --- | --- |
| Embodiment | 84% | 2% | 14% |
| Comparison | 64% | 20% | 16% |

As seen in Table 1, the data in accordance with the Embodiment of the present invention show a significant improvement in the Overkill Rate from 20% to 2% in contrast with those of the Comparison by means of the prior art boundary samples. As a result, the Correct Rate of the former is also greatly improved in comparison with that of the latter.

Correct Rate data of the embodiment method implemented by unskilled inspectors, not set forth in Table 1 though, rise remarkably in comparison with the prior art method by them so that there is a quite small Correct Rate difference between skilled and unskilled inspectors In addition, regardless of skilled or unskilled inspectors, different judgment results in the embodiment method are very small with respect to individual variations.

Next, Table 2 shows judgment results of two actually uneven sample displays on a display panel under various environmental illuminance conditions. Here, the judgments have been based on 5 mm square density patterns 21 and figures are described at dot occupied rates of the density patterns 21 to which the sample displays have looked equivalent. Table 2 sets forth the average values of results assessed by five inspectors as in Table 1.

TABLE 2

Influence of Ambient Illuminance an Density Judgment

| Ambient Illuminance | 11Lx | 40Lx | 130Lx | 195Lx |
| --- | --- | --- | --- | --- |
| Deep Density Sample | 35% | 35% | 35% | 35% |
| Light Density Sample | 5% | 5% | 5% | 5% |

There has been no influence of ambient illuminance on density judgment of samples with unevenness. In other words, the embodiment method is irrelevant to ambient illuminance of inspection places so that the inspection is firmly carried out without any specific labors to maintain uniform illuminance.

The density gauge 2 can be easily and satisfactorily made by dot printing The density levels remain unchanged unless the printed dotted patterns fall down. Thus, it is unnecessary to monitor changes in density levels. There are no visual dispersions because the density patterns are printed. In short, it is extremely easy and significantly low in cost to make, prepare and maintain standard density references.

Inspectors are not requested to remember the density of unevenness nor to have any skill for judgment because the judgment is made with the inspection gauge 1 positioned on or next to a display panel. It is unnecessary to prepare display panels with actual levels of unevenness, i.e., boundary samples. The assessment can be carried out by the same assessment criteria in a plurality of sites. Since both unevenness and the inspection gauge are subject to the same ambient illuminance conditions or rear light conditions when the inspection gauge 1 is placed on the unevenness, the judgment or assessment for density is not influenced by such illuminance conditions or rear light conditions. In other words, since the assessment of optical unevenness can be made by the same conditions at the same time, the present invention increases reliabilities for density judgments and reduces dispersions for density assessments.

Desired levels of density can be easily realized by setting dot occupied rates. Thus, it is quickly and flexibly adaptive to change sizes and specifications of display panels. Since density levels are expressed in numerical figures based on dotted area occupied rates, density data can be compiled by objective assessments.

A period of time to judge unevenness is shortened remarkably so that inspection efficiency can be greatly improved.

Judgment for the density of unevenness can be carried out with high accuracy and reliability regardless of skillfulness of inspectors or different working conditions.

Obviously many modifications and variations to the present invention are possible in light of the above teachings. It is therefore to be understood that within the scope of the appended claims the invention may be practiced otherwise than as specifically described. The present invention is applicable not only a display device but also an optical device to project an area light output. For example, it is applicable to assess optical unevenness of a light projection surface in an illumination apparatus, e.g., ant area light source.

As set forth above in detail, the present invention remarkably improves the accuracy of assessment of optical unevenness.

What is claimed is:

1. A method of inspecting an optical device, comprising:
   placing an inspection gauge on a main surface of said optical device, said inspection gauge being provided with a density pattern formed on a transparent sheet or film; and
   comparing optical unevenness of said optical device with said density pattern of said inspection gauge in light of a density degree to determine whether said optical unevenness is lighter or darker in density than or equal to said density pattern of said inspection gauge.

2. The method according to claim 1, wherein said optical device projects light from said main surface when said optical device is enabled.

3. The method according to claim 1, wherein said inspection gauge is placed on said main surface of said optical device in order for said density pattern to be next to said optical unevenness.

4. The method according to claim 1, wherein said inspection gauge is placed on said main surface of said optical device in order for said density pattern to cover said optical unevenness.

5. The method according to claim 1, wherein said inspection gauge includes a plurality of different degree of density patterns.

6. The method according to claim 5, wherein said different degree of density patterns are disposed in order of density degrees.

7. The method according to claim 6, wherein said different degree of density patterns are applied in said order of density degrees to said optical unevenness for comparison with said optical unevenness or for inspection as to whether a difference between said different degree of density patterns and said optical unevenness is visible or not.

8. The method according to claim 1, wherein at least one of said density patterns is made of dots provided on said sheet or film and said density degree is expressed by a rate of dots occupied per unit area.

9. The method according to claim 8, wherein said dots are discrete circles or rectangles which are uniformly dispersed.

10. The method according to claim 8, wherein said dots are of a predetermined size.

11. The method according to claim 8, wherein said dots are less than or equal to 40 $\mu$m in size.

12. The method according to claim 8, wherein said inspection gauge includes density patterns with different dot occupied rates and said dot occupied rates range from 3% through 45%.

13. The method according to claim 12, wherein said density patterns of said inspection gauge include low density levels each defined by a discretely additional and predetermined dot occupied rate ranging from 1% to 3% and high density levels each defined by a discrete additional dot occupied rate of 5%.

14. The method according to claim 1, wherein said optical device is a display panel.

15. The method according to claim 1, wherein said optical device is an illumination apparatus.

16. An inspection gauge to assess optical unevenness on a main surface of an optical device, comprising:
a transparent base sheet or film; and
a density pattern provided on said base sheet or film,
wherein said density pattern is made of a set of dots which are less than or equal to 40 $\mu$m in size.

* * * * *